(12) United States Patent
Fukai et al.

(10) Patent No.: US 7,428,293 B2
(45) Date of Patent: Sep. 23, 2008

(54) FLUORESCENT X-RAY ANALYSIS APPARATUS

(75) Inventors: Takayuki Fukai, Chiba (JP); Yoshiki Matoba, Chiba (JP)

(73) Assignee: SII Nanotechnology Inc., Chiba (JP)

( * ) Notice: Subject to any disclaimer, the term of this patent is extended or adjusted under 35 U.S.C. 154(b) by 0 days.

(21) Appl. No.: 11/729,247

(22) Filed: Mar. 28, 2007

(65) Prior Publication Data

US 2008/0013681 A1      Jan. 17, 2008

(30) Foreign Application Priority Data

Mar. 30, 2006 (JP) .............................. 2006-094116
Feb. 7, 2007 (JP) .............................. 2007-028448

(51) Int. Cl.
*G01N 23/223* (2006.01)
*G21K 1/02* (2006.01)

(52) U.S. Cl. .............................. 378/44; 378/46; 378/147

(58) Field of Classification Search ............ 378/44–49, 378/70, 86–90, 147–150, 156–159
See application file for complete search history.

(56) References Cited

U.S. PATENT DOCUMENTS 6,337,897 B1 * 1/2002 Kawahara et al. ............. 378/45

FOREIGN PATENT DOCUMENTS

JP     2004-150990     5/2004

* cited by examiner

*Primary Examiner*—Irakli Kiknadze
(74) *Attorney, Agent, or Firm*—Brinks Hofer Gilson & Lione

(57) ABSTRACT

There is provided a fluorescent X-ray analysis apparatus in which a detection lower limit has been improved by reducing an X-ray generating subsidiarily and detected. The fluorescent X-ray analysis apparatus is one which possesses an X-ray source irradiating a primary X-ray, and a detector in which a collimator having a through-hole in its center part has been placed in a front face, and in which, by the detector, there is detected a primary fluorescent X-ray which generates from a sample by irradiating the primary X-ray to a sample, and passes through the through-hole of the collimator. The X-ray source and the detector are disposed while adjoining the sample, and an irradiated face of the X-ray source or the detector, to which a primary scattered ray having generated by the fact that the primary X-ray scatters in the sample and the primary fluorescent X-ray having generated from the sample are irradiated, is covered by a secondary X-ray reduction layer reducing a secondary scattered ray and a secondary fluorescent X-ray, which generate by irradiations of the primary scattered ray and the primary fluorescent X-ray.

15 Claims, 4 Drawing Sheets

FLUORESCENT X-RAY ANALYSIS APPARATUS

RELATED APPLICATIONS

This application claims priority under 35 U.S.C. §119 to Japanese Patent Application Nos. JP2006-094116 filed Mar. 30, 2006 and JP2007-028448 filed Feb. 7, 2007, the entire content of which is hereby incorporated by reference.

BACKGROUND OF THE INVENTION

1. Field of the Invention

The present invention relates to a fluorescent X-ray analysis apparatus which performs an element analysis and a composition analysis of a sample by irradiating a primary X-ray to the sample and detecting a fluorescent X-ray generating from the sample.

2. Description of the Related Art

In recent years, a cadmium pollution of a food, and the like become a problem, and a quantitative determination of a cadmium content in the food, and the like are performed. Hitherto, in the quantitative determination of cadmium, although there have been performed an ICP (inductively coupled plasma spectrometry) and the like, there have been problems that, in addition to the fact that a time is necessary for such a pretreatment as to make the sample into a solution, a dispersion occurs in a measurement result in dependence on an operator. From the background like this, as a measurement method substituted for the ICP, a fluorescent X-ray analysis is noted. The fluorescent X-ray analysis is one in which a kind and a quantity of an element contained in the sample is specified by irradiating the primary X-ray to the sample and detecting the generated fluorescent X-ray, and hitherto it has been utilized mainly in an analysis of the sample, such as Cu alloy or Fe alloy, whose main component is a heavy element, and the like. Since the fluorescent X-ray has an intensity and an energy which are inherent to the element, it is possible to specify the element having been contained in the sample and its quantity by detecting an intensity and an energy of the generated fluorescent X-ray. In the fluorescent X-ray analysis, there suffices if the primary X-ray is directly irradiated to the sample, and there are advantages that a measurement is possible even if the sample is not pretreated and, also as to an analysis result, a reproducibility is good in comparison with the ICP. A detection lower limit denoting an accuracy of the fluorescent X-ray analysis like this is determined by the following expression.

Detection lower limit=$3 \times (\sqrt{\text{Background intensity}/\text{Measurement time}})/\text{Sensitivity}$ Here, the background intensity means mainly an intensity of a scattered X-ray or the like other than the fluorescent X-ray generating from an aimed element having been contained in the sample. Further, the sensitivity is a magnitude of an X-ray intensity obtainable in a detector. That is, by decreasing the background intensity and further raising the sensitivity, the detection lower limit is improved, and it becomes possible to realize the quantitative determination of a trace element.

As the fluorescent X-ray analysis apparatus capable of performing the fluorescent X-ray analysis like this, for example, there is proposed one having possessed an X-ray source irradiating the primary X-ray to the sample, a detector detecting the fluorescent X-ray generated from the sample to which the primary X-ray has been irradiated, and a primary filter having plural filter components, or the like (e.g., refer to JP-A-2004-150990 Gazette). According to the fluorescent X-ray analysis apparatus like this, by absorbing the primary X-ray of plural energy bands by the primary filter and irradiating the primary X-ray of a necessary energy band, it is possible to decrease the background intensity, thereby improving the detection lower limit.

However, the primary X-ray having been irradiated to the sample excites the sample to thereby generate the fluorescent X-ray (primary fluorescent X-ray) and, by the sample, scatters to a periphery as a primary scattered ray. And, between the primary fluorescent X-ray and the primary scattered ray, one part having been not detected by the detector generates, by the fact that it is irradiated to an X-ray source, an outer periphery face of the detector or the like, a secondary X-ray. That is, by the fact that it scatters in the X-ray source, the outer periphery face of the detector or the like, a secondary scattered ray generates and, further by the fact that it excites elements forming the X-ray source, the outer periphery face of the detector or the like, a secondary fluorescent X-ray generates. And, one part of the X-ray having been generated secondarily scatters directly or again in the sample and is detected by the detector. That is, by the fact that the unnecessary X-ray having generated subsidiarily, which is the X-ray other than the primary fluorescent X-ray to be detected originally, is detected by the detector, a count (intensity) of the X-ray entering into the detector increases. In a case like this, since there is a limit in the count of the X-ray capable of being detected by the detector, although it is necessary to suppress the intensity of the primary X-ray irradiated from the X-ray source, the intensity of the primary fluorescent X-ray capable of being detected lowers as well, so that there has been a problem the detection lower limit deteriorates as a result. Further, by placing a member (hereafter, called a collimator), which has a through-hole, in a front face of the detector, although it is possible to suppress the count of the X-ray entering into the detector, since the secondary fluorescent X-ray generating from a hole wall of the through-hole of the collimator is detected in its most by the detector, the count of the X-ray is increased by this X-ray generating secondarily, so that it is impossible to fundamentally reduce the X-ray other than the primary fluorescent X-ray to be detected originally.

Further, in a count circuit, by the fact that the count increases in such a degree that the X-rays having generated subsidiarily cannot be discriminated as separate ones, a count error (hereafter, called a pileup) occurs. The pileup exerts two adverse effects on a spectrum obtainable. One is a deterioration (a peak width of the spectrum becomes thick) of an energy resolving power. The other one is the fact that a pseudo-peak called "sum-peak" is formed. Both increase the background intensity, thereby deteriorating the detection lower limit. From the problem like this, as mentioned above, although there is noted the quantitative determination of the trace aimed element such as the cadmium content in the food, due to these X-rays generating subsidiarily, there has not led to obtain the detection lower limit under which the quantitative determination of the trace aimed element is possible.

SUMMARY OF THE INVENTION

This invention is one having been made in view of the above-mentioned circumstances, and one providing a fluorescent X-ray analysis apparatus in which the detection lower limit has been improved by reducing the X-ray generating subsidiarily and detected.

In order to solve the above problems, this invention proposes the following means.

The present invention is a fluorescent X-ray analysis apparatus which possesses an X-ray source irradiating a primary X-ray, and a detector in which a collimator having a through-hole in its center part has been placed in a front face, and in which, when the primary X-ray has been irradiated to a sample from the X-ray source, a primary fluorescent X-ray generating from the sample and passing through the through-hole of the collimator is detected by the detector, wherein the X-ray source and the detector are disposed while adjoining the sample, and an irradiated face of the X-ray source or the detector, to which a primary scattered ray having generated by the fact that the primary X-ray scatters in the sample and the primary fluorescent X-ray having generated from the sample are irradiated, is covered by a secondary X-ray reduction layer reducing a secondary scattered ray and a secondary fluorescent X-ray, which generate by irradiations of the primary scattered ray and the primary fluorescent X-ray.

According to the fluorescent X-ray analysis apparatus concerned with this invention, while the primary X-ray having been irradiated to the sample from the X-ray source excites the sample to thereby generate the primary fluorescent X-ray, it scatters by the sample to a periphery as the primary scattered ray. One parts of the primary fluorescent X-ray and the primary scattered ray pass through the through-hole of the collimator, and are detected by the detector. And, since the primary fluorescent X-ray having been detected has an energy inherent to an element contained in the sample, it is possible to quantify the element contained in the sample by that energy and the intensity. On this occasion, since the X-ray source is disposed while adjoining the sample, the primary X-ray is effectively irradiated at a high density from the X-ray source without being attenuated. Additionally, since the detector is disposed while adjoining the sample as well, the primary fluorescent X-ray having generated is effectively detected at a high density without being attenuated.

On the other hand, one parts of the primary scattered ray and the primary fluorescent X-ray, which don't pass through the through-hole, are irradiated to the above-mentioned irradiated face. On this occasion, by the fact that the irradiated face is covered by the secondary X-ray reduction layer, these X-rays are absorbed to the secondary X-ray reduction layer, and it is possible to reduce a scattered ray (hereafter, referred to as a secondary scattered ray) generating secondarily by scattering in the irradiated face, and a fluorescent X-ray (hereafter, referred to as a secondary fluorescent X-ray) generating secondarily by the fact that an element forming the irradiated face is excited. That is, the secondary scattered ray and the secondary fluorescent X-ray, which generate, or a scattered ray (hereafter, referred to as a tertiary scattered ray) generating by the fact that the former rays are irradiated again to the sample and scatter in the sample pass or passes through the through-hole of the collimator, and thus it is possible to reduce the intensity of the X-ray detected by the detector. Therefor, it is possible to suppress the pileup resulting from an increase in the X-ray having generated subsidiarily, such as the secondary scattered ray, the secondary fluorescent X-ray and the tertiary scattered ray, thereby reducing a background. Further, by reducing the intensities of the secondary scattered ray, the secondary fluorescent X-ray and the tertiary scattered ray, which are detected by the detector, it is possible to reduce the count (intensity) of the unnecessary X-ray entering into the detector. Therefor, it is possible to increase the intensity of the primary X-ray irradiated to the sample and, by this, it is possible to increase the intensity of the primary fluorescent X-ray generating from the sample, thereby raising the sensitivity.

Further, it is deemed to be more desirable that, in the above fluorescent X-ray analysis apparatus, the secondary X-ray reduction layer is formed by an element whose energy of a fluorescent X-ray generating in maximum from the secondary X-ray reduction layer is lower than an energy of a fluorescent X-ray generating in maximum from an irradiated face having been covered by the secondary X-ray reduction layer.

That is, according to the fluorescent X-ray analysis apparatus concerned with this invention, by the fact that the primary scattered ray and the primary fluorescent X-ray are irradiated to the secondary X-ray reduction layer, the secondary X-ray reduction layer is excited, so that the secondary fluorescent X-ray generates also from the secondary X-ray reduction layer. However, since the secondary fluorescent X-ray generating from the secondary X-ray reduction layer is lower in its energy than the secondary fluorescent X-ray generating from the irradiated face, the secondary fluorescent X-ray generating from the secondary X-ray reduction layer is suppressed as mentioned above. Further, there can be made a lower energy with respect to the primary fluorescent X-ray becoming an object of a measurement, so that it is possible to reduce the background intensity.

Additionally, it is deemed to be more desirable that, in the above fluorescent X-ray analysis apparatus, the secondary X-ray reduction layer is constituted by at least two layers of a base layer and a surface layer covering the base layer, and the surface layer is formed by an element whose energy of a fluorescent X-ray generating in maximum from the surface layer is lower than an energy of a fluorescent X-ray generating in maximum from the base layer.

According to the fluorescent X-ray analysis apparatus concerned with this invention, by being constituted by at least two layers of the base layer and the surface layer, the primary scattered ray and the primary fluorescent X-ray, which are irradiated to the irradiated face, are absorbed stepwise by the surface layer and the base layer whose absorption efficiency is higher. Additionally, by covering the base layer by the surface layer, since the energy of the secondary fluorescent X-ray generating from the secondary X-ray reduction layer can be made a lower energy, the secondary fluorescent X-ray generating from the secondary X-ray reduction layer is suppressed as mentioned above. Further, there can be made the lower energy with respect to the primary fluorescent X-ray becoming the object of the measurement, so that it is possible to reduce the background intensity.

Further, it is deemed to be more desirable that, in the above fluorescent X-ray analysis apparatus, the secondary X-ray reduction layer covers a hole wall of the through-hole of the collimator.

According to the fluorescent X-ray analysis apparatus concerned with this invention, the primary fluorescent X-ray and the primary scattered ray, which have entered into the through-hole of the collimator, pass through the through-hole and are directly entered into the detector, and their one parts are irradiated to the hole wall of the through-hole. On this occasion, since the secondary X-ray reduction layer is provided in the hole wall of through-hole, it is possible to reduce the secondary fluorescent X-ray generating from the hole wall of the through-hole, thereby reducing the count of the unnecessary X-ray entering into the detector.

Further, it is deemed to be more desirable that, in the above fluorescent X-ray analysis apparatus, the secondary X-ray reduction layer covers an outer periphery face of the collimator.

According to the fluorescent X-ray analysis apparatus concerned with this invention, the primary fluorescent X-ray and the primary scattered ray, which have been irradiated to the outer periphery face of the collimator, are absorbed to the secondary X-ray reduction layer, and thus it is possible to reduce the secondary scattered ray and the secondary fluorescent X-ray, which are irradiated again to the sample. Therefor, it is possible to reduce the tertiary scattered ray generating by the fact that the secondary scattered ray and the secondary fluorescent X-ray scatter in the sample, so that the background intensity can be reduced, and the count of the unnecessary X-ray entering into the detector can be reduced.

According to the fluorescent X-ray analysis apparatus of the present invention, by covering the irradiated face by the secondary X-ray reduction layer, it is possible to absorb the primary fluorescent X-ray and the primary scattered ray, which are irradiated to the irradiated face, thereby reducing the X-ray generating subsidiarily, such as the secondary scattered ray and the secondary fluorescent X-ray. Therefor, it is possible to suppress an increase in the count of the detector, which results from these unnecessary X-rays generating subsidiarily, increase the intensity of the primary fluorescent X-ray obtainable with respect to the X-ray generating subsidiarily, and raise the sensitivity, thereby contriving an improvement in the detection lower limit.

DETAILED DESCRIPTION OF THE PREFERRED EMBODIMENT

Figure 1:
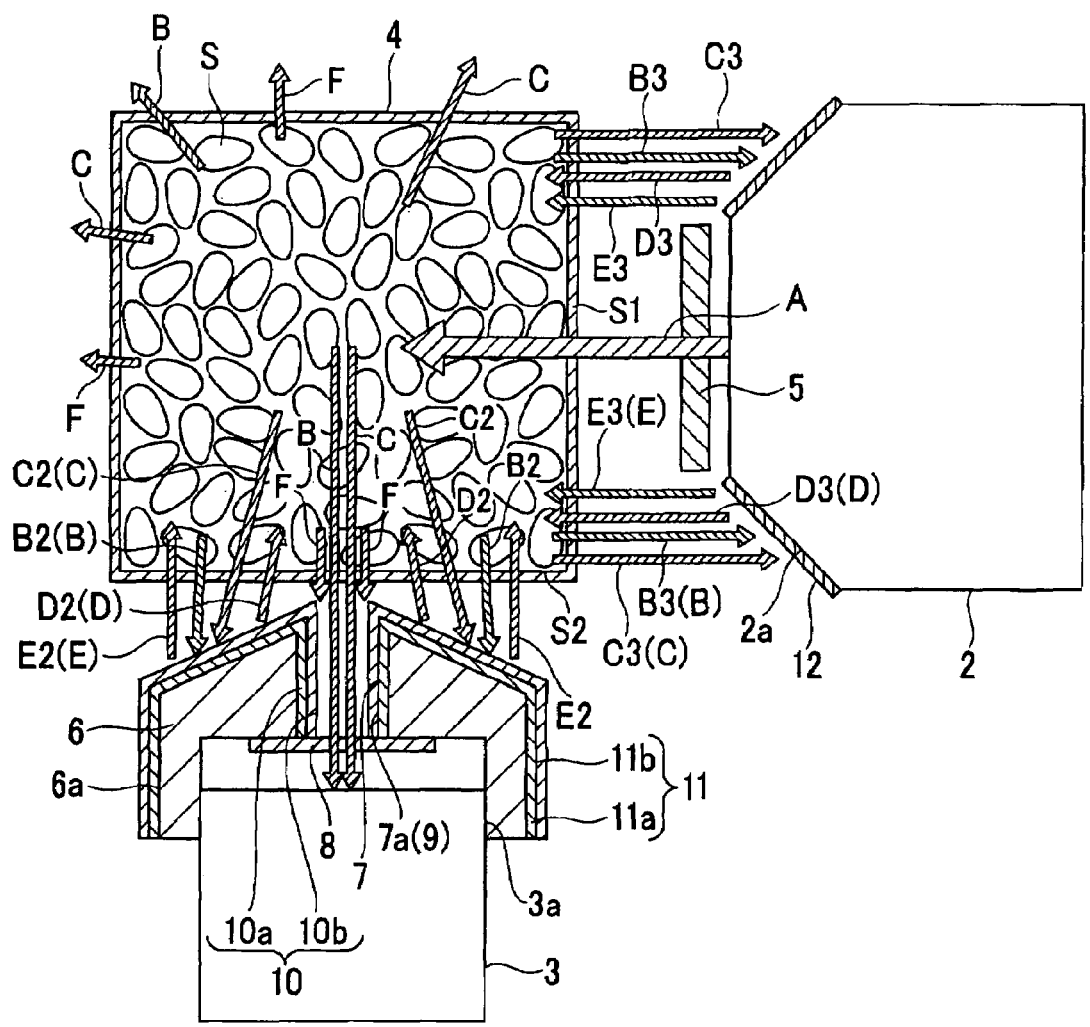
FIG. 1 is a sectional view of a fluorescent X-ray analysis apparatus of an embodiment of this invention.

FIG. 1 to FIG. 4 show an embodiment concerned with this invention. As shown in FIG. 1, a fluorescent X-ray analysis apparatus possesses an X-ray source 2 disposed while adjoining one face S1 of a sample S and irradiating a primary X-ray A to the sample S, and a detector 3 disposed adjoining the other face S2 of the sample S and detecting a primary fluorescent X-ray B generating from the sample S. The sample S is a solid or as liquid, which has a fluidity, and enclosed in a container 4 having been formed by a material capable of transmitting an X-ray. More detailedly, in the present embodiment, the sample S is a granular rice, and it is one attempting to quantify Cd contained in the rice. The X-ray source 2 is an X-ray tube bulb for instance, and one irradiating the primary X-ray A having been constituted by a characteristic X-ray and a continuous X-ray of a target of the X-ray tube bulb. In the present embodiment, an outer hull of the X-ray source 2 is formed by brass having been composed of Cu and Zn.

In front of the X-ray source 2, a primary filter 5 is provided in a position through which the irradiated primary X-ray A passes. The primary filter 5 is one absorbing only the X-ray of a specified energy within the primary X-ray A irradiated from the X-ray source 2. And, by absorbing the X-ray of the same energy range as the fluorescent X-ray B generating from the aimed element (element to be quantified) having been contained in the sample S, it is possible to improve the detection lower limit by suppressing an increase in the count and an increase in the background intensity due to the fact that the X-ray other than the fluorescent X-ray B is detected.

The detector 3 can detect an energy and an intensity of the fluorescent X-ray B generating from the sample S. A collimator 6 is covered to a tip part 3a of the detector 3. The collimator 6 is one suppressing an increase in the count of the X-ray entered into the detector 3, and a member in which a through-hole 7 has been formed in its center part. The collimator 6 is formed by such a heavy element that the X-ray other than that entered from the through hole 7 is not transmitted, and it is Mo for instance. Further, a secondary filter 8 is provided in an inside opening 7a of the through-hole 7 of the collimator 6, and the X-ray having been entered into the through-hole 7 passes through the secondary filter 8 and is detected by the detector 3. The secondary filter 8 is one absorbing, within the X-ray entered into the through-hole 7, only an X-ray of a specified energy range. And, by absorbing an X-ray of an energy range different from the fluorescent X-ray B generating from the aimed element having been contained in the sample S, the detector 3 can detect a fluorescent X-ray of a specified energy, and it is possible to suppress the count of the X-ray to be detected, thereby raising a detection efficiency.

By the fact that the primary X-ray A is irradiated to the sample S from the X-ray source 2, the primary X-ray A is absorbed in its one part to the sample S, scattered in its one part by the sample S, and its one part excites the sample S to thereby generate the fluorescent X-ray. And, these X-rays pass through the through-hole 7 of the collimator 6 to thereby be detected by the detector 3, and are irradiated to an irradiated face 9 that is other exposed portion. As the irradiated face 9, there are an outer periphery face 2a of the X-ray source 2, an outer periphery face 6a of the collimator 6, and a hole wall 7a of the through-hole 7 of the collimator 6. And, these irradiated faces 9 are covered respectively by secondary X-ray reduction layers 10, 11 and 12. The secondary X-ray reduction layer 10 covering the hole wall 7a of the through-hole 7 of the collimator 6 is constituted by two layers of a base layer 10a covering the hole wall 7a of the through-hole 7 of the collimator 6 and a surface layer 10b covering the base layer 10a. The base layer 10a is formed by an element whose energy of the fluorescent X-ray generating in maximum is lower than an energy of the fluorescent X-ray generating in maximum (in highest intensity) from Mo forming the collimator 6, and it is Cu for instance.

Here, there is explained about a reason why, in a case where the collimator is formed by Mo, Cu (copper) is used as the base layer 10a of the secondary X-ray reduction layer 10.

There are known the facts that, in a certain element, a generation efficiency of the fluorescent X-ray generating from the sample by the primary X-ray having been irradiated from the X-ray source becomes higher the more an energy of the primary X-ray having been irradiated is than an absorption end energy of the element generating the fluorescent X-ray and nearer to the absorption end energy, and that, if the energy of the primary X-ray having been irradiated is lower than the absorption end energy of the element generating the fluorescent X-ray, the generation efficiency becomes zero (0).

Here, the absorption end energy of a K shell of Cu is 8.98 keV, and the absorption end energy of an L shell is LI absorption end 1.100 keV, LII absorption end 0.953 keV and LIII absorption end 0.933 keV.

And, in a case where an energy of the primary X-ray having been irradiated to Cu is higher than the absorption end energy of the K shell of Cu, e.g., in a case where it is 50 keV, from the above conditions of the generation efficiency, a K ray that is the fluorescent X-ray from the K shell generates more than an L ray that is the fluorescent X-ray from the L shell. On the other hand, in a case where the energy of the X-ray having been irradiated to Cu is lower than the absorption end energy of the K shell of Cu, and higher than the absorption end energy of the L shell of Cu, e.g., in a case where it is 7 keV, it follows that the K ray does not generate and only the L ray generates. In a case where the energy of the primary X-ray having been irradiated to Cu is lower than the absorption end energy of the L shell, both of the K ray and the L ray don't generate.

Further, the absorption end energy of a K shell of Mo is 17.4 keV, and the absorption end energy of an L shell is LI absorption end 2.88 keV, LII absorption end 2.62 keV and LIII absorption end 2.52 keV.

Whereupon, like the present embodiment, by the fact that a surface of the collimator 6 composed of Mo is covered by the base layer 10a of the secondary X-ray reduction layer composed of Cu, the primary scattered and the primary fluorescent X-ray, which generate in the sample, are absorbed to the base layer 10a of the secondary X-ray reduction layer and, by that fact that the primary scattered ray and the primary fluorescent X-ray which excite the collimator 6 reduce, the secondary fluorescent X-ray and the secondary fluorescent X-ray which generate from the collimator 6 reduce. In addition, the secondary fluorescent X-ray generating from the collimator 6 is absorbed by passing again through the base layer 10a of the secondary fluorescent X-ray reduction layer, and thus the secondary fluorescent X-ray generating from the collimator 6 is additionally reduced. By the above processes, although the secondary fluorescent X-ray and the secondary scattered ray, which generate from the collimator 6, are reduced, instead of it, the secondary fluorescent X-ray and the secondary scattered ray generate from the base layer 10a of the secondary X-ray reduction layer.

However, in a case where the energies of the primary scattered ray and the primary fluorescent X-ray are higher than the absorption end energy of the K shell of Mo, e.g., in a case where they have been made 50 keV, from the above conditions of the generation efficiency, since the generation efficiency of the secondary fluorescent X-ray generating from the base layer 10a of the secondary X-ray reduction layer becomes lower than the secondary fluorescent X-ray generating from the collimator 6 when there is no base layer 10a of the secondary X-ray reduction layer, it is possible to reduce the secondary fluorescent X-ray.

By this, by the fact that the secondary X-ray reduction layer is formed by an element whose absorption end energy of the fluorescent X-ray generating in maximum from the secondary X-ray reduction layer is lower than the absorption end energy of the fluorescent X-ray generating in maximum from the irradiated face having been covered by the secondary X-ray reduction layer, it is possible to effectively reduce the secondary fluorescent X-ray in a case where the primary fluorescent X-ray and the primary scattered ray, which have generated from the sample, are larger than the absorption end energy.

Further, as to the detector, although the secondary fluorescent X-ray is absorbed during a time till it enters into a detection element, it becomes more difficult to be detected the lower becomes the energy of the secondary fluorescent X-ray. Therefor, like the above conditions relating to the element forming the secondary X-ray reduction layer, by using the element of the secondary X-ray reduction layer so as to lower the energy of the fluorescent X-ray generating by the secondary X-ray reduction layer, it is possible to additionally reduce the secondary fluorescent X-ray.

Further, the surface layer 10b is formed by an element whose energy of the fluorescent X-ray generating in maximum is lower than the energy of the fluorescent X-ray generating in maximum from Cu forming the base layer 10a, and it is Al for instance. Further, also the secondary X-ray reduction layer 11 covering the outer periphery face 6a of the collimator 6 is constituted similarly by two layers of a base layer 11a and a surface layer 11b. And, similarly, the base layer 11a is formed by Cu, and the surface layer 11b is formed by Al which is the element whose energy of the fluorescent X-ray generating in maximum is lower than the energy of the fluorescent X-ray generating in maximum from Cu forming the base layer 11a.

Further, the secondary X-ray reduction layer 12 covering the outer periphery face 2a of the X-ray source 2 is constituted by one layer, and formed by an element whose energy of the fluorescent X-ray generating in maximum is lower than the energy of the fluorescent X-ray generating in maximum from Cu and Zn, which form the outer periphery face 2a of the X-ray source 2, and it is formed by Al for instance.

Figure 3:
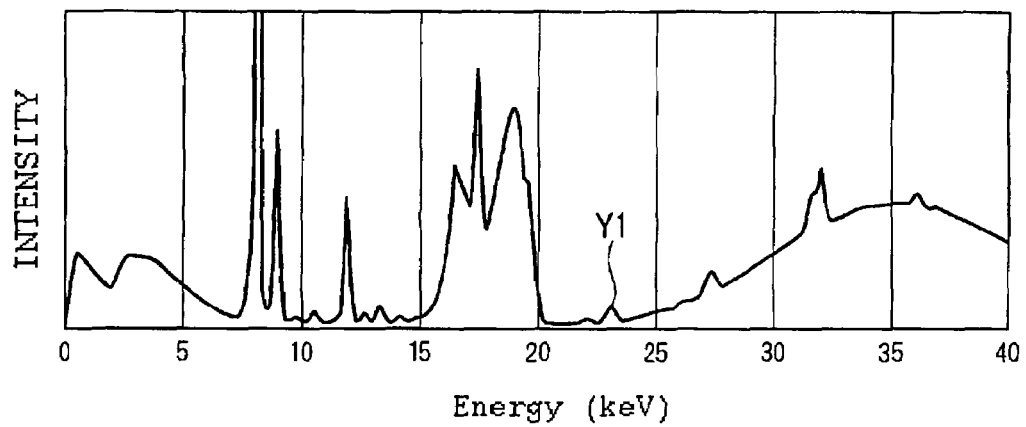
FIG. 3 is a graph showing a relation between an energy and an intensity of an X-ray having been detected in the embodiment of this invention.
Figure 4:
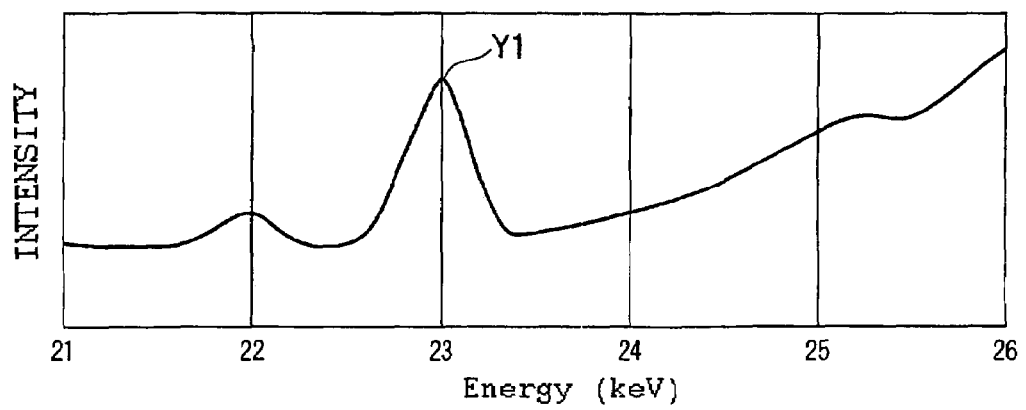
FIG. 4 is a partial enlarged view of the graph shown in FIG. 3.

Next, there are explained about actions of the fluorescent X-ray analysis apparatus 1. As shown in FIG. 1, the primary X-ray A having been irradiated from the X-ray source 2 passes through the primary filter 5, and is irradiated to the sample S while having a predetermined solid angle. On this occasion, since the X-ray source 2 is disposed while adjoining the sample S, the primary X-ray A can be irradiated to the sample S at a high density without attenuating. And, as to the primary X-ray A having been irradiated to the sample S, its one part excites an element contained in the sample S to thereby generate the fluorescent X-ray (hereafter, referred to as a primary X-ray) inherent to the element, and one part of the primary X-ray A is scattered to a periphery by the sample S as a primary scattered ray C. And, one parts of the primary fluorescent X-ray B and the primary scattered ray C pass through the through-hole 7 of the collimator 6, and are detected by the detector 3. Within the X-ray having been detected, from an energy and an intensity, which show a component of the primary fluorescent X-ray, an element contained in the sample S is specified. For example, as shown in FIG. 3 and FIG. 4, in a case where Cd of a predetermined quantity is contained in the sample S, it is possible to detect a peak Y1 of the intensity near 23 keV that is an energy range of the fluorescent X-ray of Cd. Incidentally, within the X-ray having been detected, a component of the primary scattered ray C is detected as a characteristic X-ray whose peak is formed in other energy band and a continuous X-ray continuously detected in the whole energy band of the X-ray. Further, the other primary fluorescent X-ray B and the primary scattered ray C, which don't pass through the through-hole 7 of the collimator 6, scatter to a periphery, or are irradiated to the outer periphery face 2a of the X-ray source 2, the outer periphery face 6a of the collimator 6, or the hole wall 7a of the through-hole 7, that is the irradiated face 9.

Figure 2:
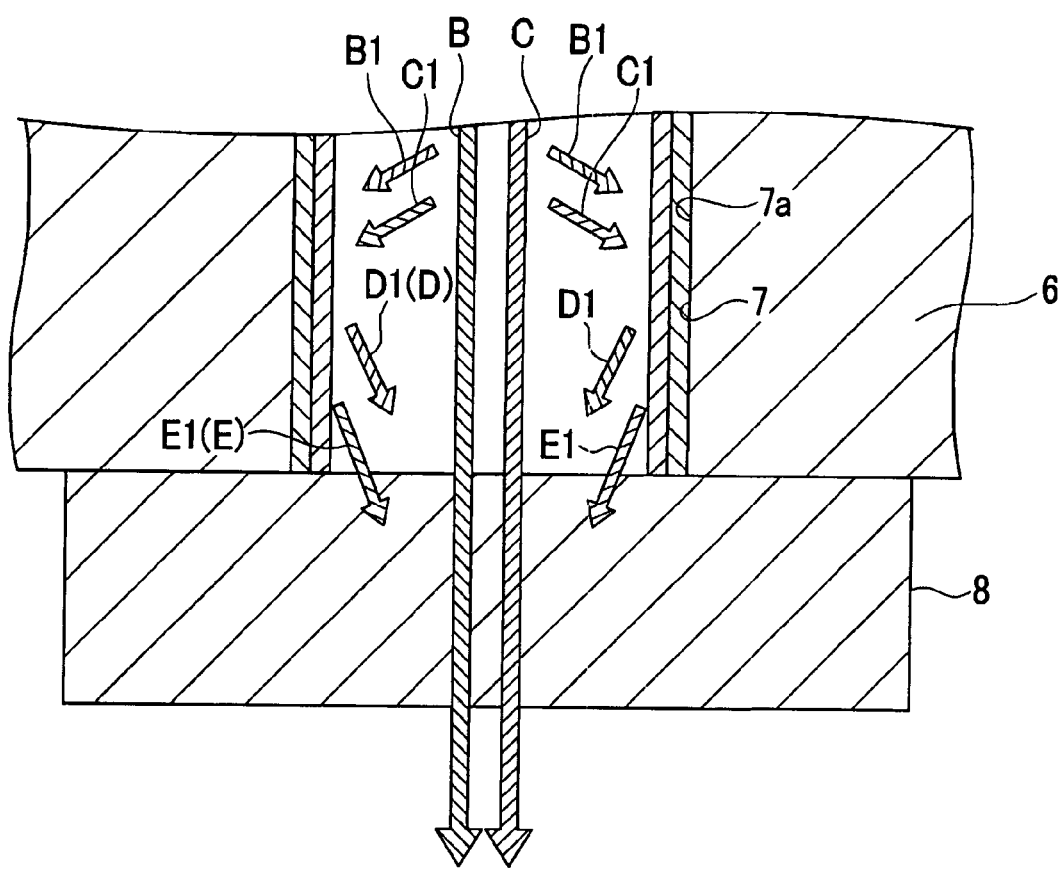
FIG. 2 is an enlarged sectional view of a portion of a collimator of the fluorescent X-ray analysis apparatus of the embodiment of this invention.

As shown in FIG. 2, a primary fluorescent X-ray B1 and a primary scattered ray C1, which are irradiated to the hole wall 7a of the through-hole 7 of the collimator 6, are absorbed stepwise by the surface layer 10b and the base layer 10a, which constitute the secondary X-ray reduction layer 10. More detailedly, first, one parts of the primary fluorescent X-ray B1 and the primary scattered ray C1 are absorbed to the surface layer 10b, and the other one parts transmit through it and irradiate the base layer 10a. Additionally, as to the primary fluorescent X-ray B1 and the primary scattered ray C1, which have been irradiated to the base layer 10a, their one parts are absorbed to the base layer 10a. Since the base layer 10a is formed by the element generating the fluorescent X-ray whose energy is higher than the surface layer 10b, it is possible to absorb the primary fluorescent X-ray B1 and the primary scattered ray C1 at a high absorption efficiency. Finally, only one parts of the primary fluorescent X-ray B1 and the primary scattered ray C1, which have transmitted through the base layer 10a, are irradiated to the hole wall 7a of the through-hole 7. That is, by the fact that many of the primary fluorescent X-ray B1 and the primary scattered ray C1, which are irradiated, are absorbed to the base layer 10a and the surface layer 10b, which constitute the secondary X-ray reduction layer 10, it is possible to reduce intensities of a secondary scattered ray D1 generating by scattering in the hole wall 7a of the through-hole 7 and a secondary fluorescent X-ray E1 generating by the fact that the element forming the hole wall 7a of the through-hole 7 is excited. Further, since the secondary fluorescent X-ray E1 having generated from the hole wall 7a of the through-hole 7 is additionally absorbed in the base layer 10a and the surface layer 10b, it is possible to additionally reduce the intensity of a secondary fluorescent X-ray E2 generating from the hole wall 7a of the through-hole 7. Further, by the fact that the primary fluorescent X-ray B1 and the primary scattered ray C1 are irradiated, the base layer 10a and the surface layer 10b are excited as well, so that the secondary fluorescent X-ray E1 generates from each of these layers. However, since the base layer 10a and the surface layer 10b are formed by the element (Cu, Al) generating the fluorescent X-ray whose energy is lower than the element (Mo) forming the collimator 6, the energy of the secondary fluorescent X-ray E1 which generates can be made a lower energy. Further, as to the secondary fluorescent X-ray E1 generating from the base layer 10a, it is reduced by being absorbed in the surface layer 10b. Like the above, by the fact that the hole wall 7a of the through-hole 7 is covered by the secondary X-ray reduction layer 10, the primary fluorescent X-ray B1 and the primary scattered ray C1 are absorbed, and it is possible to reduce the intensities of the secondary scattered ray D1 and the secondary fluorescent X-ray E1, which generate, and the energy of the secondary fluorescent X-ray E1 which generates can be made the lower energy. One of reasons why the energy of the secondary fluorescent X-ray is made the low energy is for the fact that it is possible to suppress the secondary fluorescent X-ray generating subsidiarily, because an excitation efficiency becomes worse the more the energy of the secondary fluorescent X-ray generating by the primary scattered ray and the primary fluorescent X-ray is separated to a low energy side from the energies of the primary scattered ray and the primary fluorescent X-ray. The other one is for the fact that it is possible to suppress the detection of the secondary fluorescent X-ray generating subsidiarily, because a detection efficiency of the detector becomes worse the lower becomes the energy of the X-ray.

Further, as shown in FIG. 1, a primary fluorescent X-ray B2 and a primary scattered ray C2, which are irradiated to the outer periphery face 6a of the collimator 6, are similarly absorbed stepwise in the surface layer 11b and the base layer 1a, which constitute the secondary X-ray reduction layer 11, to thereby reduce the intensities of a secondary scattered ray D2 and the secondary fluorescent X-ray E2, which generate, and the secondary fluorescent X-ray E2 can be made the lower energy. The secondary scattered ray D2 and a secondary fluorescent X-ray E2, which have generated, scatter again by the sample S, so that a tertiary scattered ray F generates. And, although one part of the tertiary scattered ray F passes through the through-hole 7 of the collimator 6 and is detected, it is possible to reduce an intensity of this tertiary scattered ray F and make it a lower energy. Reason why an energy of the tertiary scattered ray is made the low energy is because it is possible to suppress a detection of the tertiary scattered ray generating subsidiarily, since the detection efficiency of the detector becomes worse the lower becomes the energy of the X-ray.

Additionally, as shown in FIG. 1, a primary fluorescent X-ray B3 and a primary scattered ray C3, which are irradiated to the outer periphery face 2a of the X-ray source 2, are similarly absorbed by the secondary X-ray reduction layer 12. Although the secondary X-ray reduction layer 12 is constituted by one layer having been formed by Al, it is formed by the element (Al) generating the fluorescent X-ray whose energy is lower than the element (Cu, Zn) forming the outer periphery face 2a of the X-ray source 2. Therefor, similarly, it is possible to reduce intensities of a secondary scattered ray D3 and a secondary fluorescent X-ray E3, which generate, and make the secondary fluorescent X-ray E3 a low energy. As to the secondary scattered ray D3 and the secondary fluorescent X-ray E3, which have generated, their one parts directly pass through the through-hole 7 of the collimator 6 and are detected by the detector 3. Further, the other one parts scatter in the sample S and become the tertiary scattered ray F. Although one part of the tertiary scattered ray F passes through the through-hole 7 of the collimator 6 and is detected, by the fact that intensities of the secondary scattered ray D3 and the secondary fluorescent X-ray E3 are reduced and they are low energies, also the tertiary scattered ray F is additionally reduced in its intensity, and it can be made a low energy.

Figure 5:
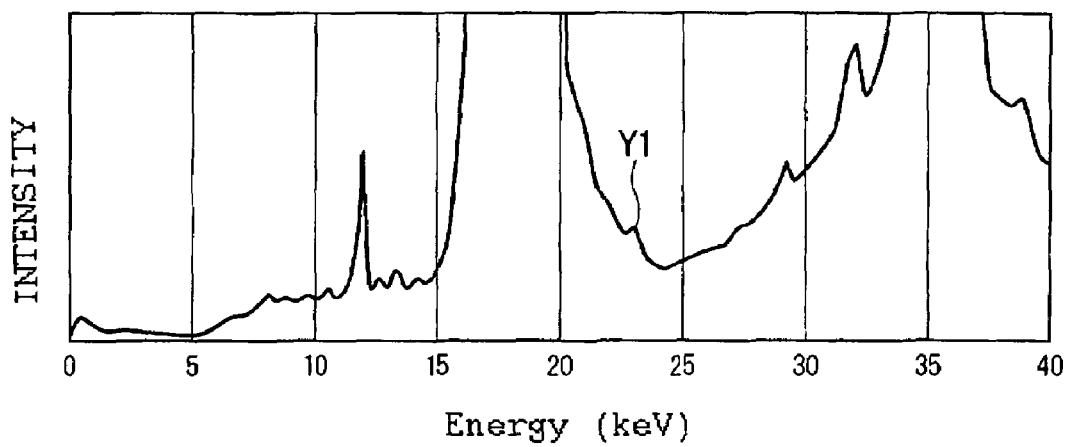
FIG. 5 is a graph showing a relation between the energy and the intensity of the X-ray having been detected in a comparative example.
Figure 6:
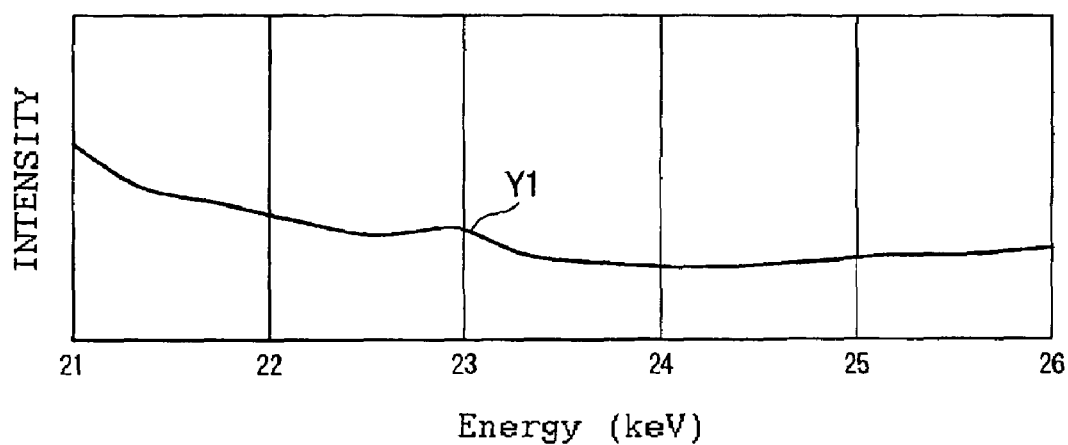
FIG. 6 is a partial enlarged view of the graph shown in FIG. 5.

Like the above, by covering the outer periphery face 2a of the X-ray source 2, the outer periphery face 6a of the collimator 6 and the hole wall 7a of the through-hole 7 of the collimator 6, which are the irradiated faces 9, by the secondary X-ray reduction layers 10, 11 and 12, it is possible to reduce the intensities of the secondary scattered ray D and the secondary fluorescent X-ray E, which generate form each irradiated face 9, and further the tertiary scattered ray F generating by the fact that the formers scatter again, thereby making them low energies. These X-rays generating subsidiarily are unnecessary X-rays differing from the primary fluorescent X-ray B generating from the element contained in the sample S, and bring about an increase in a useless count. That is, by reducing the intensities of these X-rays generating subsidiarily and making them the low energies, it is possible to suppress the increase in the count to thereby reduce the background intensity, and it is possible to contrive an improvement in the detection lower limit. FIG. 3 and FIG. 4 are measurement results in a case where the sample S containing Cd has been measured by the fluorescent X-ray analysis apparatus 1, and FIG. 5 and FIG. 6 are measurement results in a case where, as a comparative example, there has been made a constitution in which the secondary X-ray reduction layers 10, 11 and 12 are not provided. As shown in FIG. 3 and FIG. 4, the fact is seen that the fluorescent X-ray (Kα ray) of Cd can be confirmed while having the peak Y1 in the energy range of 23 keV. On the other hand, as shown in FIG. 5 and FIG. 6, in the case where the secondary X-ray reduction layers 10, 11 and 12 are not provided, as mentioned above, since the background intensity increases by the pileup in the count circuit, the peak Y1 is buried in the background, so that it becomes difficult to confirm an accurate intensity of the primary fluorescent X-ray B.

Further, by reducing the intensity of the X-ray generating subsidiarily, such as the secondary scattered ray D, the secondary fluorescent X-ray E and the tertiary scattered ray F, it is possible to reduce a count of the unnecessary X-ray detected by the detector. And, by a quantity in which the count of the unnecessary X-ray has been reduced, it is possible to increase the intensity of the primary X-ray A to thereby increase the intensity of the primary fluorescent X-ray B generating from the sample. Therefor, it is possible to raise the intensity, i.e., the sensitivity, of the primary fluorescent X-ray B, which can be obtained by the detector 3, thereby additionally improving the detection lower limit.

Additionally, in the secondary X-ray reduction layer 10 and the secondary X-ray reduction layer 11, there can be constituted by the two layers of the base layers 10a and 11a, and the surface layers 10b and 11b. Therefor, it is possible to effectively absorb the primary fluorescent X-ray B and the primary scattered ray C, which are irradiated, and the energy of the secondary fluorescent X-ray E can be made the lower energy with respect to the energy of the primary fluorescent X-ray B.

Like the above, by covering the secondary X-ray reduction layers 10, 11 and 12 to the irradiated faces 9, it is possible to improve the detection lower limit, and realize the quantitative determination of the trace aimed element, such as the quantitative determination of Cd contained in the food. Especially, in the case where the X-ray source 2 and the detector 3 have been disposed while adjoining the sample S, effects of a reduction in the background intensity and a reduction in the count of the X-ray by the secondary X-ray reduction layers 10, 11 and 12 become remarkable, so that it is possible to more effectively contrive an improvement in the detection lower limit in cooperation with an effect by being provided while adjoining.

In the above, although there has been detailedly mentioned about the embodiment of the present invention by referring to the drawings, a concrete constitution is not one limited to this embodiment, and there is included also a design modification or the like in a scope not deviating from a gist of the present invention.

Incidentally, in the present embodiment, as the irradiated faces 9, although there have been enumerated the outer periphery face 2a of the X-ray source 2, the outer periphery face 6a of the collimator 6 and the hole wall 7a of the through-hole 7 of the collimator 6, there is not limited to these. By providing the secondary X-ray reduction layer in at least a portion to which there are irradiated the primary scattered ray C and the primary fluorescent X-ray B, which generate by the primary X-ray A, it is possible to expect the similar effect. Further, although there have been made such that, about the secondary X-ray reduction layers 10 and 11, they are constituted by the two layers of Cu and Al and, about the secondary X-ray reduction layer 12, by the one layer of Al, there is not limited to these. There suffices if it is constituted by at least one layer having been formed by the element generating the fluorescent X-ray whose energy is lower than the element forming the irradiated face 9, and it may be made a constitution of three or more layers. Further, in the present embodiment, as the sample S, although one in which the solid (rice) having the fluidity has been enclosed in the container 4 has been enumerated in the example, there is not limited to this. For example, it may be other food having a certain regular shape, or other one whose main component is a light element, and it is possible to expect the effect also in a sample whose main component is a heavy element. Further, in the fluorescent X-ray analysis apparatus 1, although there has been made one in which the primary filter 5 and the secondary filter 8 are provided, there may be made a constitution in which they are not provided and, further, there may be made a constitution in which filters of different kinds can be switched at a suitable time.

What is claimed is:

1. A fluorescent X-ray analysis apparatus which possesses an X-ray source irradiating a primary X-ray, and a detector in which a collimator having a through-hole in its center part has been placed in a front face, and in which, when the primary X-ray has been irradiated to a sample from the X-ray source, a primary fluorescent X-ray generating from the sample and passing through the through-hole of the collimator is detected by the detector, wherein the X-ray source and the detector are disposed while adjoining the sample, and an irradiated face of at least one of the X-ray source and the detector, to which a primary scattered ray having generated by the fact that the primary X-ray scatters in the sample and the primary fluorescent X-ray having generated from the sample are irradiated, is covered by a secondary X-ray reduction layer reducing a secondary scattered ray and a secondary fluorescent X-ray, which generate by irradiations of the primary scattered ray and the primary fluorescent X-ray, and wherein the secondary X-ray reduction layer is formed by an element whose energy of a fluorescent X-ray generating in maximum from the secondary X-ray reduction layer is lower than an energy of a fluorescent X-ray generating in maximum from a face having been covered by the secondary X-ray reduction layer.

2. A fluorescent X-ray analysis apparatus according to claim 1, wherein the secondary X-ray reduction layer is constituted by at least two layers of a base layer and a surface layer covering the base layer, and the surface layer is formed by an element whose energy of a fluorescent X-ray generating in maximum from the surface layer is lower than an energy of a fluorescent X-ray generating in maximum from the base layer.

3. A fluorescent X-ray analysis apparatus according to claim 1, wherein the secondary X-ray reduction layer covers a hole wall of the through-hole of the collimator.

4. A fluorescent X-ray analysis apparatus according to claim 1, wherein the secondary X-ray reduction layer covers an outer periphery face of the collimator.

5. A fluorescent X-ray analysis apparatus comprising:
    an X-ray source configured to interrogate a sample with a primary X-ray;
    a detector configured to detect a fluorescent X-ray excited out from the sample;
    a collimator configured to collimate X-rays reaching the detector, the collimator being made of a first material and having a surface comprising an exterior surface defining the exterior of the collimator and an interior surface defining the interior surface of a hole for collimation; and
    an X-ray reduction layer which covers at least part of the surface of the collimator in such a manner as to reduce a disturbance on detection by the detector which is caused by X-rays other than the fluorescent X-ray, the X-ray reduction layer being made of at least one second material selected such that a fluorescent X-ray generatable most from the at least one second material has an energy lower than that of a fluorescent X-ray generatable most from the first material.

6. A fluorescent X-ray analysis apparatus according to claim 5, wherein at least part of the X-ray reduction layer comprises two layers which are laid with one on top of the other.

7. A fluorescent X-ray analysis apparatus according to claim 6, wherein the two layers are made of different materials selected such that a fluorescent X-ray generatable most from each of the two layers has an energy lower than that of an fluorescent X-ray generatable most from the first material.

8. A fluorescent X-ray analysis apparatus according to claim 6, wherein the first material is Mo, and the two layers are made respectively of Cu and Al, in which the Al layer is laid on top of the Cu layer.

9. A fluorescent X-ray analysis apparatus according to claim 5, wherein the first material is Mo, and the second material is one of Cu and Al.

10. A fluorescent X-ray analysis apparatus according to claim 5, wherein the X-ray reduction layer covers both at least part of the exterior surface and at least part of the interior surface.

11. A fluorescent X-ray analysis apparatus according to claim 10, wherein the at least one second material in the X-ray reduction layer laid over the exterior surface comprises at least one material common in the at last one second material in the X-ray reduction layer laid over the interior surface.

12. A fluorescent X-ray analysis apparatus according to claim 5, wherein the X-ray source is made of third material and covered at least in part with a second X-ray reduction layer in such a manner as to reduce a disturbance on a detection by the detector which is caused by X-rays other than the fluorescent X-ray, and the second X-ray reduction layer is made of a fourth material selected such that a fluorescent X-ray generatable most from the fourth material has an energy lower than that of a fluorescent X-ray generatable most from the third material.

13. A fluorescent X-ray analysis apparatus according to claim 12, wherein the third material comprises at least one of Cu and Zn, and the fourth material is Al.

14. A fluorescent X-ray analysis apparatus comprising:
an X-ray source configured to interrogate a sample with a primary X-ray, the X-ray source being made of a first material and having a surface;
a detector configured to detect a fluorescent X-ray excited out from the sample; and
an X-ray reduction layer which covers at least part of the surface of the X-ray source in such a manner as reduce a disturbance on detection by the detector which is caused by X-rays other than the fluorescent X-ray, the X-ray reduction layer being made of at least one second material selected such that a fluorescent X-ray generatable most from the at least one second material has an energy lower than that of a fluorescent X-ray generatable most from the first material.

15. A fluorescent X-ray analysis apparatus according to claim 14, wherein the first material comprises at least one of Cu and Zn, and the at least one second material comprises Al.

* * * * *